United States Patent
Melz et al.

(10) Patent No.: US 7,770,464 B2
(45) Date of Patent: Aug. 10, 2010

(54) DEVICE FOR DYNAMICALLY LOAD TESTING A SAMPLE

(75) Inventors: Tobias Melz, Darmstadt (DE); Michael Matthias, Darmstadt (DE); Holger Hanselka, Darmstadt (DE)

(73) Assignee: Fraunhofer-Gesellschaft zur Förderung Derangewandten Forschung E.V., Munich (DE)

( * ) Notice: Subject to any disclaimer, the term of this patent is extended or adjusted under 35 U.S.C. 154(b) by 48 days.

(21) Appl. No.: 11/813,892

(22) PCT Filed: Jan. 20, 2006

(86) PCT No.: PCT/EP2006/000514

§ 371 (c)(1),
(2), (4) Date: Jul. 13, 2007

(87) PCT Pub. No.: WO2006/077143

PCT Pub. Date: Jul. 27, 2006

(65) Prior Publication Data

US 2008/0092665 A1    Apr. 24, 2008

(30) Foreign Application Priority Data

Jan. 21, 2005    (DE) .................. 10 2005 003 013

(51) Int. Cl.
*G01N 3/32* (2006.01)
*G01N 3/08* (2006.01)

(52) U.S. Cl. ................. 73/811; 73/808; 73/813; 73/818

(58) Field of Classification Search ............ 73/808, 73/811, 813, 818; 188/266.7
See application file for complete search history.

(56) References Cited

U.S. PATENT DOCUMENTS

| 3,842,662 | A |   | 10/1974 | Key, Jr. et al. |
| 3,933,032 | A |   | 1/1976 | Tschoegl |
| 5,291,967 | A |   | 3/1994 | Aoki |
| 5,425,276 | A | * | 6/1995 | Gram et al. ............ 73/816 |
| 5,823,307 | A | * | 10/1998 | Schubert et al. .......... 188/378 |
| 6,023,980 | A |   | 2/2000 | Owen et al. |
| 6,172,445 | B1 | * | 1/2001 | Heinz et al. ............. 310/328 |

(Continued)

FOREIGN PATENT DOCUMENTS

DE    28 29 858    1/1980

(Continued)

*Primary Examiner*—Lisa M Caputo
*Assistant Examiner*—Jonathan Dunlap
(74) *Attorney, Agent, or Firm*—Antonelli, Terry, Stout & Kraus, LLP.

(57) ABSTRACT

The invention is a device for dynamically load testing a sample that comprises a bearing, to which the sample can be directly or indirectly connected in a detachable manner, as well as a counter-bearing that can be effectively connected to the sample by means of at least one actuator element. The at least one actuator element introduces dynamic mechanical loads into the sample which Act along a load path that is directed between the bearing and the counter-bearing and extends through the sample. The at least one actuator element features a multifunctional solid body conversion material system that undergoes deformations due to the supply of energy, and wherein the deformations are at least one cause for the mechanical loads occurring within the sample. The device according to the invention uses at least one actuator element that may be configured in two alternative forms.

20 Claims, 4 Drawing Sheets

U.S. PATENT DOCUMENTS

| | | | |
|---|---|---|---|
| 6,405,533 B1 * | 6/2002 | Rastegar et al. | 60/545 |
| 6,488,117 B1 * | 12/2002 | Owen | 181/112 |
| 6,601,456 B1 * | 8/2003 | Davidson et al. | 73/808 |
| 6,823,744 B2 * | 11/2004 | Ohsato et al. | 73/862.041 |
| 7,160,175 B2 * | 1/2007 | Kamiya et al. | 451/11 |
| 7,247,081 B2 * | 7/2007 | Kamiya et al. | 451/10 |
| 7,637,359 B2 * | 12/2009 | Melz et al. | 188/266.7 |
| 2002/0046564 A1 * | 4/2002 | Rastegar et al. | 60/476 |
| 2006/0225977 A1 * | 10/2006 | Melz et al. | 188/266.7 |
| 2007/0212939 A1 * | 9/2007 | Melz et al. | 439/589 |

FOREIGN PATENT DOCUMENTS

| | | | |
|---|---|---|---|
| DE | 198 20 322 A1 | | 12/1999 |
| FR | 26 80 003 | | 2/1993 |
| GB | 2 060 179 A | | 4/1981 |
| GB | 2222657 A | * | 3/1990 |
| GB | 2 367 631 A | | 4/2002 |
| JP | 61-286634 | | 12/1986 |
| JP | 61286634 A | * | 12/1986 |
| JP | 62124437 A | | 6/1987 |

* cited by examiner

DEVICE FOR DYNAMICALLY LOAD TESTING A SAMPLE

BACKGROUND OF THE INVENTION

1. Field of the Invention

The invention pertains to a device for dynamically load testing a sample that comprises a bearing, to which the sample can be directly or indirectly connected in a detachable manner, as well as a counter-bearing that can be effectively connected to the sample by means of at least one actuator element such that the at least one actuator element introduces dynamic mechanical loads into the sample which act along a load path that is directed between the bearing and the counter-bearing and extends through the sample, wherein the at least one actuator element features a multifunctional solid body conversion material system that undergoes deformations due to the supply of energy, and wherein said deformations are the cause or at least one of the causes for the mechanical loads occurring within the sample.

2. Description of the Prior Art

The constantly increasing quality requirements with respect to technical modules and components are one of the major reasons why it needs to be ensured that the applicable quality and safety standards are always observed. Numerous different test devices and test methods are known for realizing the quality assurance and the quality control, wherein specific variations consist of devices for carrying out dynamic load tests, in which technical systems, modules and components or even simple material samples can be tested with respect to their mechanical load carrying capacity. For example, such dynamic load tests make it possible to obtain information on material/component properties, material/component fatigue and crack formation or crack growth per load alternation acting upon the respective component, as well as to obtain information with respect to the dynamic structural behavior.

So-called pulsators were developed for carrying out dynamic load tests on a sample, wherein the pulsators subject samples to a more or less sinusoidal load alternation. For this purpose, the sample is fixed in a suitable clamping device on two opposite sample regions that define the load path, along which the sample is subjected to dynamic compressive and/or tensile forces. In known test devices, the dynamically varying loads acting on or in the sample are generated with actuators that operate on the basis of servohydraulic, servopneumatic or servoelectric systems.

DE 198 20 322 A1 describes a servohydraulic resonance test machine that is representative for test machines with an actuator that operates on the servohydraulic principle. One side of a sample is detachably and rigidly fixed in a stable loading frame by means of a suitably designed interface, wherein the other side of the sample is connected to the piston rod of a piston-cylinder unit by means of another interface. The cylinder unit is arranged stationary relative to the loading frame while the piston rod can be displaced relative to the loading frame in a controlled manner. The displacement of the piston rod takes place under the control of oil pressure.

DE 28 29 858 describes a pulsator, the actuator of which is based on an electromagnetic principle. The sample to be examined is clamped into a holding arrangement on one side and provided with a cap of magnetically conductive material on the other side, wherein this cap is arranged such that it is separated from an opposite electromagnetic pole by an air gap, and wherein an electromagnetic alternating field is applied between the opposite pole and the cap such that the cap connected to the sample is attracted to or repelled by the magnetic pole in the direction thereof in dependence on the orientation of the magnetic field.

The generation of alternating loads that can be induced in the respective sample to be examined is limited to a maximum frequency of approximately 100 Hz when using actuators that are based on servohydraulic, servopneumatic or servoelectric principles, namely due to their system design. Even in so-called high-frequency test systems or high-frequency resonant pulsators, for example, according to the test system described in above-cited German publication DE 28 29 858, the load alternation frequencies are typically limited to a maximum of 1000 Hz. Furthermore, high-frequency pulsators of this type only make it possible to generate monofrequent load signals such that they can only be used for so-called single-stage tests.

There also exist electrodynamic vibrators that make it possible to realize load alternation frequencies up to the acoustic range, but such vibrators that are also referred to as electrodynamic shakers are only able to induce modal or base-excited loads in the sample that do not act along a load path defined by at least two fixing points of the sample to be examined, but rather along a plane of vibration that simultaneously forms the supporting plane for the sample, in which the sample is connected to the shaker. An electrodynamic shaker of this type capable of generating load alternation frequencies up to 4000 Hz is sold, for example, by Forschungsgesellschaft Kraftfahrwesen mbH, Aachen.

New materials, structures, technical modules and components as well as systems are subject to requirements that make it necessary to utilize test systems that provide a great degree of freedom with respect to the test signals or load signals to be generated and substantially broaden the frequency range toward higher frequencies. Although the available options for controlling or regulating such highly dynamic processes represent immense challenges, they are no longer the central problem with respect to the technical devices due to the continuously increasing capacity of the computers used. On the contrary, what is currently needed is an option for coupling the technically generated load signals into the structures or samples to be tested along a predefined load path or flux in suitable form. It is therefore of the utmost importance to develop new test actuators or load application components, respectively.

GB 2 060 179 A describes a material testing device, in which one side of a material to be tested is clamped in a fixed counter-bearing and the other side is connected to an actuator unit that, in turn, is coupled to a frame connected to the fixed counter-bearing. The actuator unit has piezoelectric elements that are connected to one another in a stack-shaped manner. A corresponding electrical power supply U makes it possible for the piezoelectric elements 22 to generate high-frequency vibrations that are introduced into the sample for load testing purposes. The utilization of such an actuator makes it possible to generate load alternation frequencies to the kilohertz range.

U.S. Pat. No. 3,842,662 describes a similarly designed device, in which the sample is subjected to high-frequency vibrations by means of piezoceramic elements. Hydraulic units are additionally provided for boosting the force of pressure, wherein the hydraulic units subject the sample to an additional mechanical load in hybrid form.

In a comparable arrangement for carrying out fatigue tests on a sample in accordance with publication GB 2 367 631 A, an actuator that has, among other things, with a piezoelectric or magnetostrictive material, serves for introducing forces into a sample to be examined and for generating resonant structural vibrations therein.

SUMMARY OF THE INVENTION

The invention is based on a device for dynamically load testing a sample that comprises a bearing, to which the sample can be directly or indirectly connected in a detachable manner, as well as a counter-bearing that can be effectively connected to the sample by means of at least one actuator element such that the at least one actuator element introduces dynamic mechanical loads into the sample, preferably compressive and/or tensile forces and/or torsional forces and/or bending forces and/or shearing forces acting along a load path that is directed between the bearing and the counter-bearing and extends through the sample, namely such that loads can be coupled into the sample to be examined along a load path in the most efficient manner possible with structure-acoustic load alternation frequencies of 1000 Hz, preferably 3000 Hz and more. In addition to generating and coupling monofrequent load alternations into a sample, it is also important to generate and subject the sample to dynamic load patterns other than sinusoidal load alternations, particularly time-variable pulsed loads, etc. The required control system expenditures for generating such load patterns should be maintained as low as possible.

The invention is based on a device for dynamically load testing a sample that comprises a bearing, to which the sample can be directly or indirectly connected in a detachable manner, as well as a counter-bearing that can be effectively connected to the sample by means of at least one actuator element such that the at least one actuator element introduces dynamic mechanical loads into the sample which act along a load path that is directed between the bearing and the counter-bearing and extends through the sample, wherein the at least one actuator element features a multifunctional solid body conversion material system that undergoes deformations due to the supply of energy, and wherein the deformations are the cause or at least one of the causes for the mechanical loads occurring within the sample, with the device of the invention being a special design of the actuator element that may be realized in two alternative forms:

A first design alternative of an actuator element in accordance with the invention features the following components:

A base connecting element is connected to the counter-bearing and a load connecting element is connected to the sample in a direct or indirect manner. An energy conversion system featuring the multifunctional solid body conversion material is provided between the base connecting element and the load connecting element, wherein the energy conversion system has a predominant direction that is oriented in the direction of the load path (A). In addition, at least one prestressing element extends between the base connecting element and the load connecting element, wherein the prestressing element exerts a mechanical prestress upon the energy conversion system. At least one shear force diverting element furthermore extends between the base connecting element and the load connecting element, wherein the shear force diverting element features a two-dimensional element that is arranged perpendicular to the predominant direction and realized, in particular, in the form of a membrane or leaf spring. The base connecting element is connected to the two-dimensional element by means of at least one connecting element and these interconnected elements are connected to the load connecting element by means of at least one second connecting element, wherein the first and the second connecting element are connected to the two-dimensional element on regions that do not overlap one another in a projection on the load path (A).

The functions of the prestressing element and of the shear force diverting element are advantageously fulfilled by one and the same component.

A second design alternative of the actuator element in accordance with the invention features the following components:

A base connecting element is connected to the counter-bearing and a load connecting element is connected to the sample in a direct or indirect manner. At least one support element is connected to the base connecting element by means of at least one prestressing device. At least one first energy conversion system featuring a multifunctional solid body conversion material extends between at least one application point that lies on the base connecting element and at least one application point that lies on the load connecting element. At least one second energy conversion system featuring a multifunctional solid body conversion material furthermore extends between at least one application point that lies on the support element and at least one application point that lies on the load connecting element. In this case, the base connecting element is connected to the at least one support element by means of the at least one prestressing device in such a way that the prestressing device exerts a prestress upon the first and the second energy conversion system. The load connecting element features a part that lies in the intermediate space between the base connecting element and the support element and a part that lies outside the intermediate space between the base connecting element and the support element.

The invention is characterized in two alternatively designed actuator elements, wherein a first alternative features the following components: a base connecting element is connected to the counter-bearing and a load connecting element is connected to the sample in a direct or indirect manner. An energy conversion system featuring the multifunctional solid body conversion material is provided between the base connecting element and the load connecting element, wherein the energy conversion system has a predominant direction that is oriented in the direction of the load path (A). In addition, at least one prestressing element extends between the base connecting element and the load connecting element, wherein the prestressing element exerts a mechanical prestress upon the energy conversion system. At least one shear force diverting element furthermore extends between the base connecting element and the load connecting element, wherein the shear force diverting element features a two-dimensional element that is arranged perpendicular to the predominant direction and realized, in particular, in the form of a membrane or leaf spring. The base connecting element is connected to the two-dimensional element by means of at least one connecting element and these interconnected elements are connected to the load connecting element by means of at least one second connecting element, wherein the first and the second connecting element are connected to the two-dimensional element on regions that do not overlap one another in a projection on the load path (A).

The prestressing device preferably features a tube that encloses the energy conversion systems.

Particularly suitable among the group of multifunctional solid body conversion materials are piezoceramic, electrostrictive or magnetostrictive materials that experience a change of state or shape under the influence of a well controlled magnetic or electrical field, wherein this change of state or shape can be purposefully utilized as a displacement or dynamic effect. The multifunctional material-specific process has very high dynamics, no mechanical wear and a high control accuracy and can be used for realizing a change in length or force within a suitably designed actuator, namely similar to a load application unit that is designed in accordance with the servohydraulic actuator principle, but with significantly improved wear and control characteristics and while reaching acoustic structural load alternation frequencies in the form of sinusoidal or other load alternation patterns.

According to the description that refers to diverse embodiments, it is possible to realize high-dynamic load testing devices that have only one actuator featuring a multifunctional solid body conversion material, wherein it would also be conceivable to realize hybrid load testing devices comprising a conventionally designed actuator that serves for generating load alternations with subacoustic load alternation frequencies and utilizes a multifunctional solid body conversion material, as well as a high-dynamic actuator according to the invention, and wherein the multifunctional solid body conversion material makes possible generation of highly dynamic load alternations, that is, load alternation frequencies greater than 1000 Hz with freely selectable load alternation patterns (and the option to deviate from sinusoidal loads).

Due to the high inherent rigidity of the solid body conversion materials, for example, piezoceramic materials, such actuator materials can be directly integrated into the load path of the test device in order to directly introduce compressive and/or tensile forces and/or torsional forces and/or bending forces and/or shearing forces into the sample that extends along the load path and is usually clamped between a bearing and a counter-bearing, namely by means of a correspondingly controlled length change.

The above-described natural rigidity makes it possible to integrate multifunctional solid body conversion materials into generally known actuator units along the load path in a serial or parallel manner, particularly when using hybrid load testing devices of the above-described type. This in turn makes it possible to substantially broaden the attainable frequency range of conventional actuator systems that operate in accordance with the servohydraulic or servopneumatic principle toward higher test frequencies. Consequently, the experimental structural evaluation of the samples or technical components can be significantly expanded with respect to the structural durability and the determination of characteristics, as well as with respect to the dynamic and acoustic structural characterization.

BRIEF DESCRIPTION OF THE DRAWINGS

The invention is described below in an exemplary manner with reference to embodiments that are illustrated in the figures, namely without thereby restricting the general object of the invention. In these figures.

DESCRIPTION OF THE PREFERRED EMBODIMENTS

Figure 1:
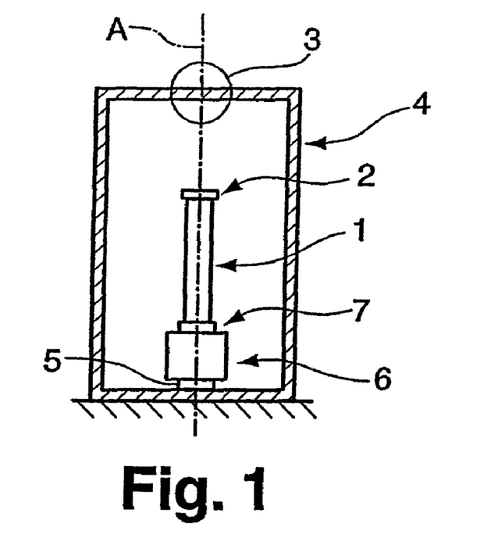
FIG. 1 shows a schematic representation of the design of a load testing device with a high-dynamic actuator in the load path.

FIG. 1 shows a schematic representation of a device for dynamically load testing a sample 1 that has an elongated shape and is connected to a bearing 3 on one side by means of a detachable interface 2. In this context, the term "bearing" refers to a mounting point that is fixed in space and situated in the upper region of a stable test or mounting frame 4 in the embodiment shown. The test frame 4 is realized in the form of a closed frame construction and features a lower counter-bearing 5 that is positioned opposite of the upper bearing 3, wherein a high-dynamic actuator element 6 is fixed on the counter-bearing, preferably by means of a rigid detachable connection. The high-dynamic actuator element 6 is furthermore connected to the sample 1 in the load path A by means of an interface 7 that lies opposite to the interface 2 and is also realized in the form of a rigid detachable connection.

For reasons of simplicity, it is assumed that the schematically illustrated actuator element 6 has entirely or partially a multifunctional solid body conversion material, preferably a piezoceramic. The solid body conversion material is connected to an a.c. voltage U or an power source (not illustrated) in order to obtain the electrical energy supply. The piezoceramic material within the high-dynamic actuator element 6 is oriented in such a way that the piezoceramic experiences length changes in the form of material extensions and contractions along the load path A due to the supply of electrical energy causes the sample clamped between the two interfaces 2 and 7 to be respectively compressed or extended in dependence on the length change of the piezoceramic material.

In contrast to conventional actuator elements that are based on the servohydraulic or servopneumatic principle and feature a multitude of individual components that mechanically cooperate with one another, the high-dynamic actuator element does not feature any moving parts that could thusly be subjected to wear. The effect causing the length change of the piezoceramic material rather is based on material-intrinsic state changes that occur spontaneously, without inertia and without wear in a controlled manner.

In addition to the utilization of piezoelectric ceramic materials, the length changes which can be induced in the presence of electrical fields, it would also be conceivable to use electrostrictive or magnetostrictive materials such as, for example, ceramic materials or metals, the deformability of which is based on change of applied electrical or magnetic fields. It would furthermore be conceivable to use shape memory alloys (shape memory materials) that are able to change their shape when external thermal energy is purposefully supplied. However, the deformation behavior of the latter-mentioned material group under multifunctional solid body conversion materials is subject to greater time constants such that their utilization for realizing a high-dynamic actuator element would be possible, in principle, but presumably result in limited test dynamics at this time.

In addition to realizing high-dynamic load testing devices, the only actuator element which causes load alternations and features a multifunctional solid body material, is suitable for being combined with a conventional, generally known actuator, for example, with a servohydraulic actuator element.

Figure 2:
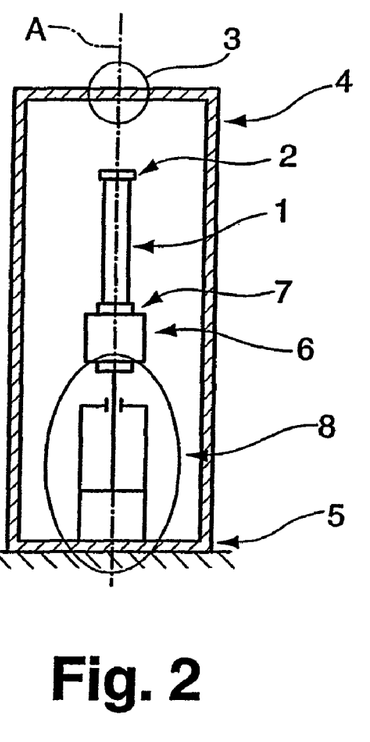
FIG. 2 shows a schematic representation of a load testing device with a conventional actuator and with a high-dynamic actuator in the flux.

Such a prior art embodiment is illustrated in FIG. 2. A sample 1 is once again situated within a test frame 4 such that one side is connected to a bearing 3 by means of a rigid detachable interface 2 and the other side is connected to a high-dynamic actuator element 6 by means of an interface 7. The conventional actuator element 8 that is based, for example, on a servohydraulic, servomechanic or servopneumatic principle is provided directly underneath the actuator element 6 in the load path A. The generally known actuator element 8 is connected to the test frame 4 that serves as the counter-bearing 5. The high-dynamic actuator element 6, as well as the generally known actuator element 8, are serially arranged in succession along the load path A and act upon the sample 1 in a superimposed manner. The hybrid serial arrangement of two actuator elements 6 and 8 according to FIG. 2 makes it possible to introduce load alternation frequencies that cover the entire load spectrum into the sample in the form of dynamic tensile and compressive forces within the sample. The load alternations in the lower frequency range that are realized with the conventionally designed actuator element 8, as well as load alternations with frequencies in the structure-acoustic range, that is, loading frequencies above the frequency range of the actuator element 8 of conventional design, for example, >1,000 Hz, are generated by the actuator element 6 featuring the multifunctional solid body conversion material up to the acoustic range and beyond.

Figure 3:
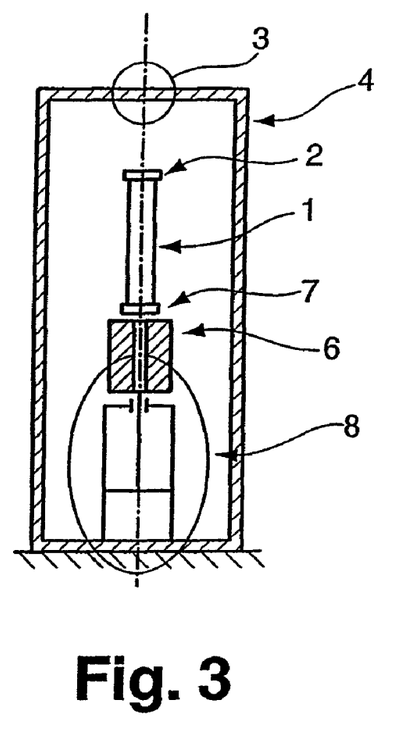
FIG. 3 shows a schematic representation of a load testing device with a conventional actuator that is supplemented with a high-dynamic actuator that acts parallel to the load path.

FIG. 3 shows a prior art dynamic load testing device that is also implemented in a hybrid manner, wherein one side of the sample 1 is connected to the bearing 3 of the test frame 4 by means of the interface 2 and the other side of the sample is connected to the high-dynamic actuator element 6 as well as an actuator element 8 of conventional design by means of the interface 7. In contrast to the embodiment shown in FIG. 2, the actuator elements 6 and 8 according to FIG. 3 act upon the sample in a parallel manner with a uniform flux along the load path A.

The above-described embodiments elucidate the modular design of a dynamic load testing device that is able to generate a uniaxial, highly dynamic load for a sample. It would be possible, in principle, to modularly supplement existing test devices with the serial or parallel utilization of a high-dynamic actuator element 6 in accordance with the invention such that the thus far conventional test frequencies can be expanded into the structure-acoustic range and beyond.

The ensuing figures show high-dynamic actuator elements of the invention that are particularly suitable for use in high-dynamic load testing devices.

Figure 4:
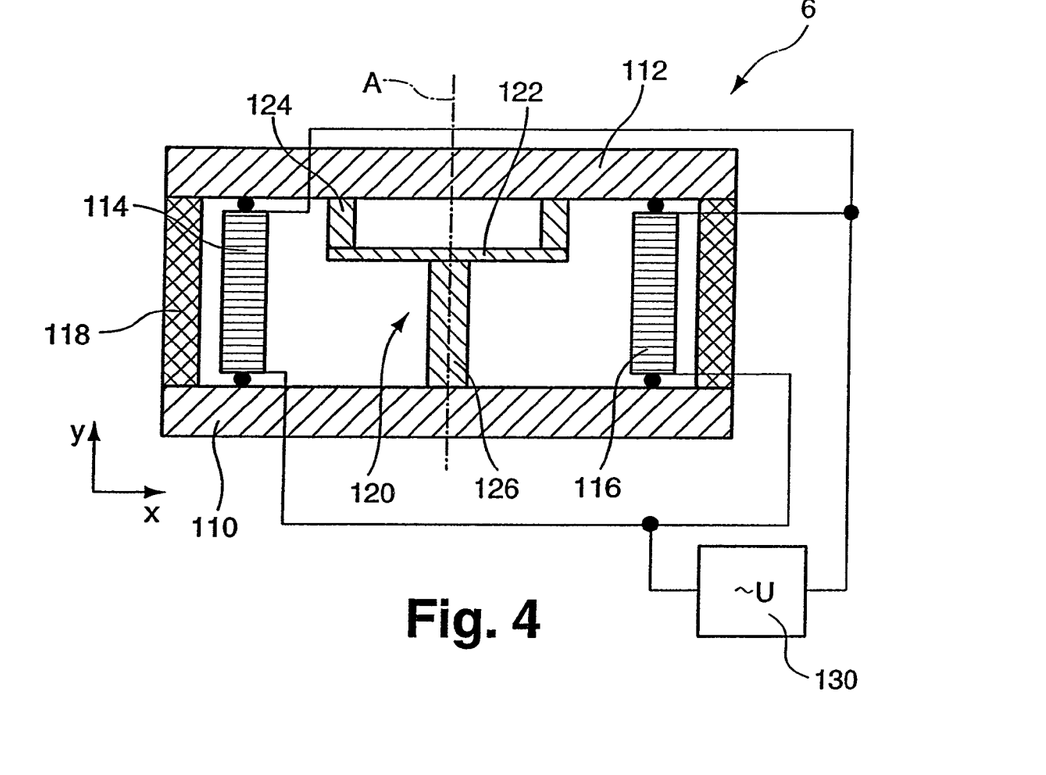
FIG. 4 shows an embodiment of a high-dynamic loading actuator in accordance with a first embodiment of the invention.

FIG. 4 shows an embodiment of an actuator element 6 for generating controlled mechanical vibrations, by means of which tensile and compressive forces can be coupled into a sample along a load path A to subject the sample to test vibrations. The actuator element 6 features a base connecting element 110 and a load connecting element 112. Both elements 110 and 112 serve as interfaces for producing a connection with the sample and with the counter-bearing, that is, the counter-bearing 5 of the prior art can be coupled with the base connecting element 110 and the sample can be coupled with the load connecting element 110 (not shown).

Actuators 114 and 116 of piezoelectric conversion material respectively extend between the base connecting element 110 and the load connecting element 112. The base connecting element 110 and the load connecting element 112 are connected by a tubular prestressing element 118 of PVC that subjects the piezoelectric actuators 114, 116 to pressure (prestress). The base connecting element 110 is furthermore connected to the load connecting element 112 by means of a shear force diverting element 120. The shear force diverting element 120 features a membrane 122 in the form of a circular disk of spring steel sheet or leaf spring. This membrane 122 is a two-dimensional element which is connected to the load connecting element 112 along its circumference by means of an annular connecting element 124. The center of the membrane 122 is connected to the base connecting element 110 by means of a second, cylindrical connecting element 126 that has a high shear modulus if shearing occurs in the direction perpendicular to the y-axis.

The shear force diverting element 120 protects the respective piezoelectric actuators 114 and 116 from shear forces acting perpendicular to its predominant direction (y-direction in FIG. 4). The membrane or leaf spring 122 is a two-dimensional element which has a high flexibility in the y-direction and a high rigidity in directions perpendicular thereto (for example, in the x-direction).

The prestressing element 118 subjects the piezoelectric actuators 114 and 116 to a constant prestress that is adjusted in such a way that the piezoelectric actuators 114 and 116 are protected from loads such as tensile forces, bending forces, torsional forces or shearing forces and operate optimally in accordance with their respective design. The prestressing element 118 is implemented in a tubular manner and completely encloses the piezoelectric actuators 114 and 116 such that moisture or dirt cannot reach the piezoelectric actuators 114 and 116.

The piezoelectric actuators 114, 116 are also protected against direct mechanical influences, for example, against impacts. Alternatively, the tubular prestressing element 118 may also be omitted. In this case (not shown), the shear force diverting element 120 simultaneously fulfills the function of prestressing the piezoelectric actuators 114 and 116. The length of the connecting element 126 is adjusted (for example, correspondingly shortened) such that the length of the shear force diverting element 120 is shorter than the length of the piezoelectric actuators 114 and 116 in the idle state. This causes pressure to be exerted upon the piezoelectric actuators 114 and 116.

Both piezoelectric actuators 114 and 116 are respectively connected to an electrical a.c. voltage source or power source 130 in order to excite vibrations, wherein electrical alternating potential of a.c. voltage or power source U causes the actuators 114 and 116 to change their length in a controlled manner such that the base connecting element 110 and the load connecting element 112 experience alternating position changes referred to the y-axis that ultimately generate tensile and compressive forces within the sample.

If the actuators 114 and 116 are displaced symmetrically and synchronously, only forces that are directed parallel to the load path A are generated such that the sample is uniaxially extended and compressed. However, additional moments of force that are tilted about the load path A or moments of force that rotate about the load path A can also be generated by controlling the actuators 114 and 116 in an asynchronous and asymmetric manner. This makes it necessary to electrically control the piezoelectric actuators 114 and 116 differently such that they are also extended differently. The load connecting element 112 is then tilted relative to the base connecting element 110 and able to carry out a tilting movement if it is controlled accordingly. Torsional vibrations, tipping motions or wobbling motions can also be generated if additional piezoelectric actuators are annularly arranged around the load path A.

Figure 5:
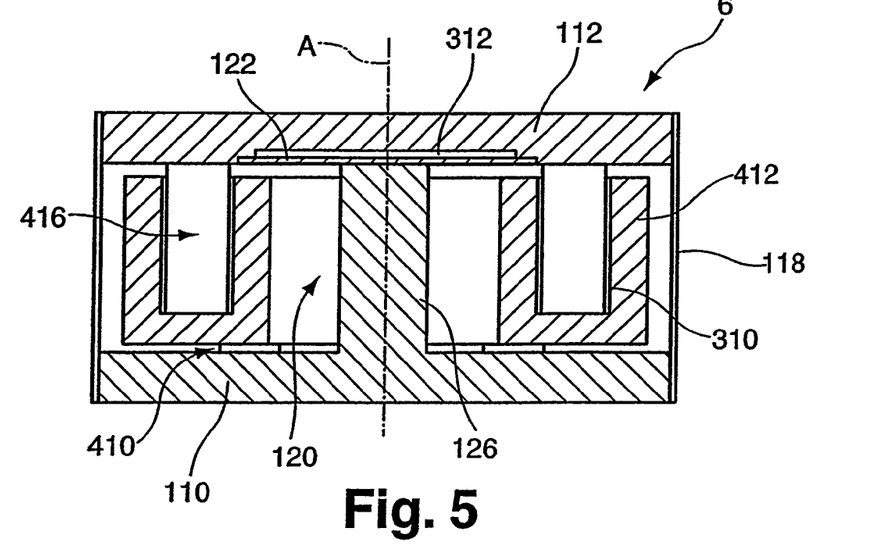
FIGS. 5 and 6 show a cross-section and an exploded view of a high-dynamic loading actuator in accordance with another embodiment of the invention.
Figure 6:
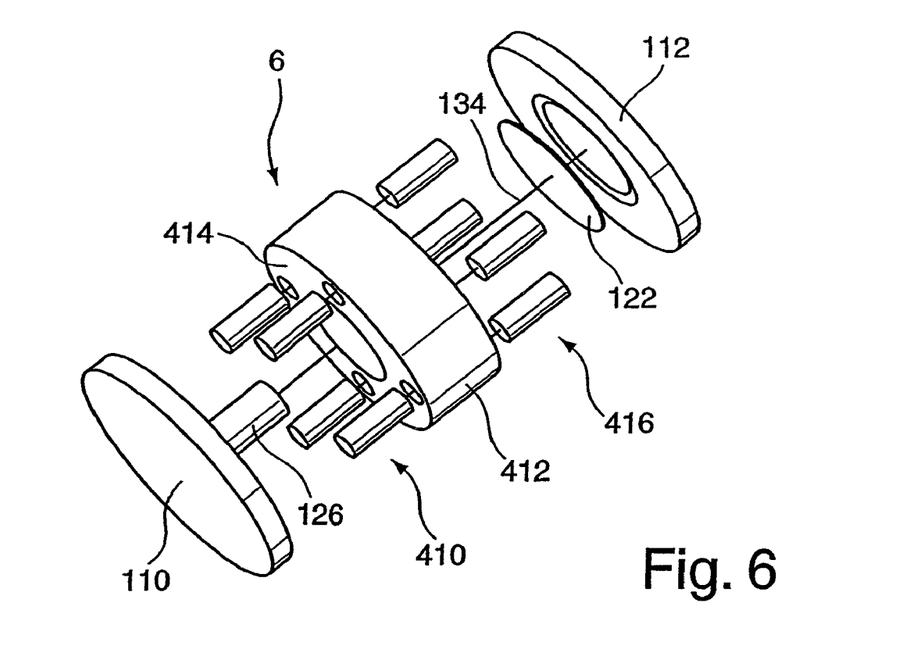

FIG. 5 (sectional representation) and FIG. 6 (exploded view) show a preferred embodiment of a cylindrical actuator element that represents an alternative to FIG. 4. The actuator element 6 features a base connecting element 110, a load connecting element 112, the tubular prestressing element 118 and a shear force diverting element 120 with a cylindrical connecting element 126 and a circular metal membrane 122. The function of the shear force diversion is identical to that of the embodiment according to FIG. 4. However, the piezoelectric actuator system is divided into two parts in this embodiment: a first piezoelectric actuator system 410 that has four actuators annularly arranged around the symmetry axis or the load path A extending between the base connecting element 10 and the coupling element 412 that is arranged between the base connecting element 110 and the load connecting element 112. This coupling element 412 is implemented in the form of a circular ring for blind bores 414 that are open toward the base connecting element 110 and are arranged in the lower flat side of the coupling element 412, wherein the piezoelectric actuators of the first piezoelectric actuator system 410 are inserted into these blind bores.

A second piezoelectric actuator system 416 extends accordingly between the load connecting element 112 and the coupling element 412. The second piezoelectric actuator system 416 once again has four individual piezoelectric actuators that are symmetrically arranged around the symmetry axis/ load path A, wherein the piezoelectric actuator system 416 is turned by 45° relative to the arrangement of the piezoelectric actuator system 410. The second piezoelectric actuator system 416 is also partially inserted into corresponding blind bores 310 in the upper plane surface of the coupling element 412.

The first and the second piezoelectric actuator systems 410 and 416 overlap because the blind bores 310 and 414 are respectively turned by 45°. The distance between the base connecting element 110 and the load connecting element 112 therefore is smaller than the sum of the structural length of a piezoelectric actuator of the first piezoelectric actuator system 410 and the structural length of a piezoelectric actuator of the second piezoelectric actuator system 416. This causes the displacement of the interface to increase in relation to an interface without coupling element 412 while the distance between the base connecting element 110 and the load connecting element 112 remains unchanged.

In this embodiment, the membrane 122 is fixed on the load connecting element 112 similar to the embodiment illustrated in FIG. 4, wherein the connecting element 124 in the shape of a circular ring was omitted. A flat cylindrical milled recess 312 is instead arranged in the load connecting element 112 and the membrane 122 is mounted over the milled recess. The membrane 122 is bonded to the load connecting element 112 along its edge.

Figure 7:
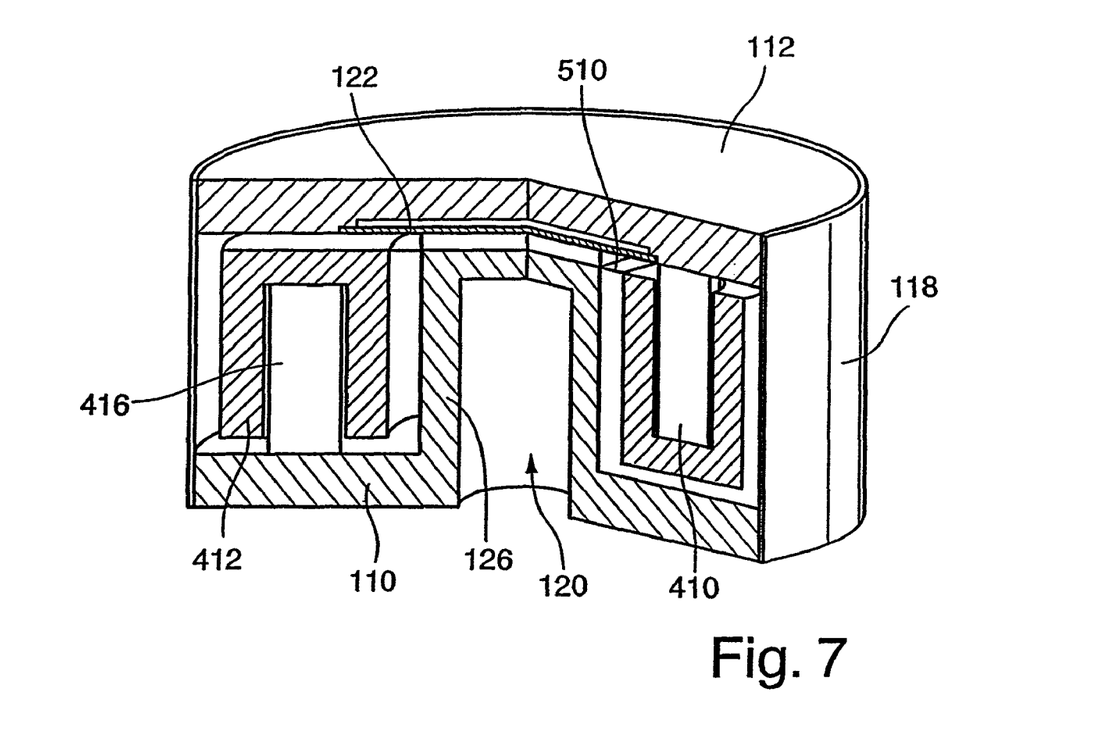
FIG. 7 shows a perspective sectional representation of a high-dynamic loading actuator in accordance with another embodiment of the invention.

FIG. 7 shows another alternative embodiment of an actuator element for exciting vibrations in the form of a partial perspective representation with cut-out segment. The design essentially is implemented similar to the embodiments illustrated in FIG. 5 and FIG. 6. However, the connecting element 126 of the shear force diverting element is implemented in the form of a hollow cylinder in this case. This saves additional space because a control unit (for example, for an active vibration control) can be accommodated, for example, in the hollow space of the connecting element 126. The membrane 122 for diverting the shear is centrally screwed to the connecting element 126. FIG. 7 also shows a centering element 510 in the form of another circular metal membrane. This membrane is bonded to the coupling element 412 in the shape of a circular ring along its circumference. In its center, the membrane 510 is screwed into the connecting element 126 in order to form the base connecting element 110. The membrane 122 prevents the coupling element 412 from changing its position relative to the connecting element 126 perpendicular to the predominant direction but allows a displacement of the coupling element 412 in the predominant direction along the load path A.

Figure 8:
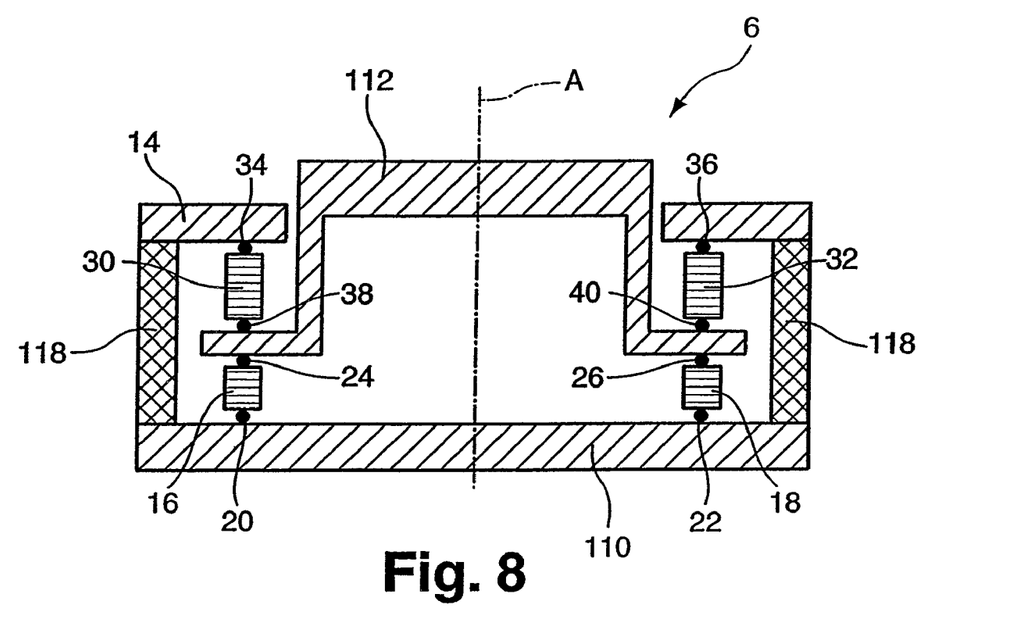
FIGS. 8 and 9 show a further embodiment of a high-dynamic loading actuator in accordance with the invention.

FIG. 8 shows another preferred embodiment of an actuator element 6. A base connecting element 110 is connected to a support element 14 by means of a prestressing device 118. A first energy conversion system having piezo actuators 16 and 18 extends between the application points 20 and 22 on the base connecting element 110 and the application points 24 and 26 on the load connecting element 112. A second energy conversion system having the piezo actuators 30 and 32 extends between the application points 34 and 36 on the support element 14 and the application points 38 and 40 on the load connecting element 112.

The illustrated arrangement shows a cross section through the structure-mechanical actuator element 6. With the exception of the piezo actuators 16, 30, 18, 32, the arrangement of this embodiment is implemented symmetrically with reference to the symmetry axis that also corresponds to the load path A. The base connecting element 110 consequently has a circular disk and the support element 14 is a ring. The load connecting element 112 has a shape that resembles a top-hat, wherein one part of the load connecting element 112 is situated in the intermediate space between the prestressing device 118 and the base connecting element 110 and another part is situated outside this intermediate space. The prestressing device 118 has an elastic tube with a diameter that is identical to the outside diameter of the circular disk of the base connecting element 110 and the outside diameter of the ring of the support element 14. Prestressing is produced by choosing the length of the elastic tube such that the tube is extended in the idle state of the arrangement. A compressive prestress is simultaneously exerted upon all piezo actuators due to this measure.

It is also possible to utilize more than the four piezo actuators as shown. These piezo actuators are preferably arranged rotationally and symmetrically to the symmetry of axis/load path A.

The base connecting element 110 and the load connecting element 112 are implemented such that the actuator element 6 can be easily and quickly mounted, for example, between a counter-bearing 5 and the sample 1. (See, for example, FIG. 1).

The distance between the load connecting element 112 and the base connecting element 110 is increased if the piezo actuators 16 and 18 are extended due to identical electrical controls and the piezo actuators 30 and 32 are shortened by the same amount due to suitable electrical controls. The distance between the load connecting element 112 and the base connecting element 110 is accordingly reduced by shortening the piezo actuators 16 and 18 and simultaneously extending the piezo actuators 30 and 32. The electrical controls of the piezo actuators are not illustrated in greater detail in the figures, but respectively require a suitable connection to an a.c. voltage source.

If the piezo actuators 16 and 30 as well as 18 and 32 are respectively controlled in phase opposition, for example, with a sinusoidal a.c. voltage of suitable amplitude and frequency, the load connecting element 112 vibrates up and down relative to the base connecting element 110.

Figure 9:
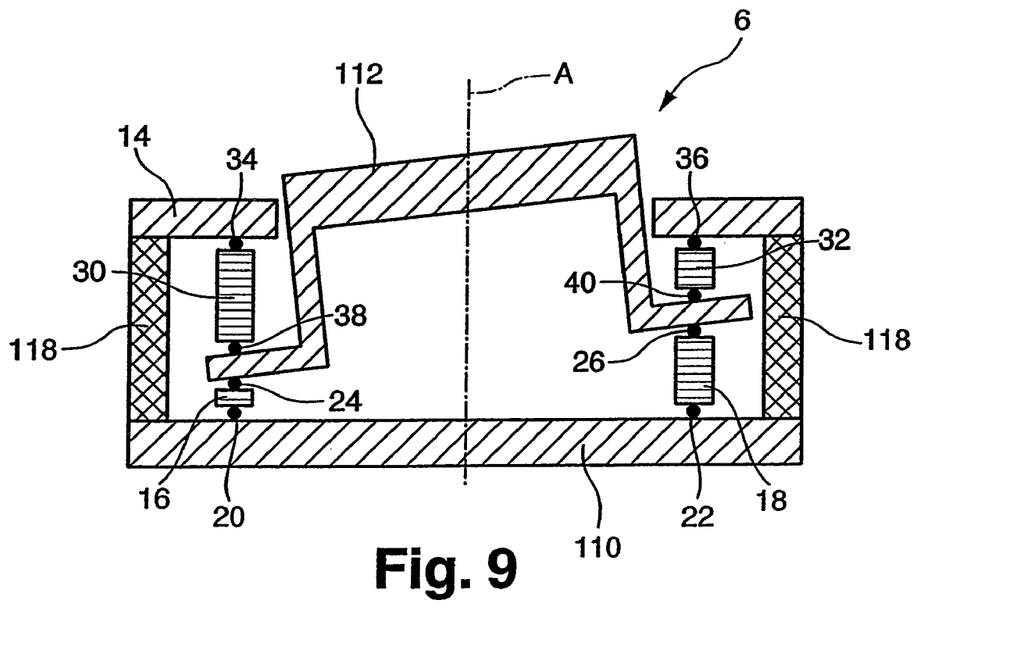

FIG. 9 shows how a purposeful control of the piezo actuators 16, 18, 30, 32 of the arrangement shown in FIG. 8 also makes it possible to excite relaxation vibrations of the base connecting element 110 relative to the load connecting element 112. The load connecting element 112 is tilted relative to the plane of the base connecting element 110 by adjusting the piezo actuator 30 to a greater length than the piezo actuator 32 with a suitable electrical control signal and accordingly adjusting the piezo actuator 16 to a shorter length than the piezo actuator 18. The piezo actuators 16, 18, 30, 32 require individual electric controls (not shown) in such instances.

LIST OF REFERENCE SYMBOLS

1 Sample
2 Interface
3 Bearing
4 Test frame, mounting frame
5 Counter-bearing
6 High-dynamic loading actuator, actuator element
7 Interface
8 Conventional actuator element
14 Support element
16 Piezo actuator
18 Piezo actuator
20 Application point
22 Application point
24 Application point
26 Application point
38 Piezo actuator
32 Piezo actuator
34 Application point
36 Application point
38 Application point
40 Application point
110 Base connecting element
112 Load connecting element
114 Piezoelectric actuator
116 Piezoelectric actuator
118 Prestressing device
120 Shear force diverting element
122 Membrane
124 Connecting element
126 Connecting element
130 A.c. voltage source
310 Blind bore
312 Cylindrical milled recess
410 First piezoelectric actuator system
412 Coupling element
414 Blind bore
416 Second piezoelectric actuator system
510 Centering element

The invention claimed is:

1. A device which provides dynamic load testing of a sample, comprising a bearing, to which the sample can be connected, and a counter-bearing to which the sample can be connected by at least one means for actuating so that the at least one means for actuating introduces dynamic mechanical loads into the sample acting along a load path directed between the bearing and the counter-bearing and extending through the sample which subjects the sample to vibrations produced by the at least one means for actuating providing the dynamic load testing of the sample, wherein the at least one means for actuating includes a solid body conversion material system which undergoes deformations in response to application of energy, and wherein the deformations are at least one cause of the mechanical loads occurring within the sample during the dynamic testing thereof, and wherein
the at least one means for actuating produces the vibrations for providing the dynamic load testing of the sample, comprises:
a) a base connecting element;
b) a load connecting element;
c) at least one energy conversion system extending between the base connecting element and the load connecting element including a solid body conversion material, with a predominant direction oriented in a direction of the load path;
d) at least one prestressing element extending between the base connecting element and the load connecting element, and exerting a mechanical prestress upon the at least one energy conversion system; and
e) at least one shear force diverting element extending between the base connecting element and the load connecting element; and wherein:
e1) the at least one shear force diverting element is flexible along the load path, is rigid in directions perpendicular to the load path and includes a two-dimensional element disposed perpendicular to the predominant direction;
e2) the base connecting element is connected to the two-dimensional element by at least one connecting element;
e3) the load connecting element is connected to the two-dimensional element by at least one second connecting element;
e4) the first and the second connecting elements are connected to the two-dimensional element at non-overlapping regions; and
e5) the base connecting element is connected to the counter-bearing and the load connecting element is connected to the sample by an interface including a rigid detachable connection.

2. The device according to claim 1, wherein:
the at least one energy conversion system comprises at least two systems each including a solid body conversion material and a coupling element;
at least one of the at least one energy conversion systems extends between the base connecting element and the coupling element; and
at least one of the at least one energy conversion systems extends between the coupling element and the load connecting element.

3. The device according to claim 1 wherein:
the at least one shear force diverting element comprises a membrane or a leaf spring.

4. The device according to claims 1, wherein
the solid body conversion material comprises a piezoceramic, an electrostrictive or a magnetostrictive material.

5. The device according to claim 1, wherein
the solid body conversion material comprises an electrostrictive, a magnetostrictive ceramic, a shape memory, or a shape memory alloy material, or a combination thereof.

6. The device according to claim 1, wherein:
electrical energy from an electrical energy source is applied to the solid body conversion material, or
a permanent magnetic field or alternating electromagnetic field is applied to the solid body conversion material.

7. The device according to claim 1, wherein:
the solid body conversion material system receives energy from an energy supply causing deformation periodically occurring within a frequency range of 1000 and 20,000 Hz.

8. The device according to claim 7 wherein:
the frequency range is between 1000 and 4000 Hz.

9. The device according to claim 1, wherein:
the bearing and the counter-bearing are spatially fixed; and at least one means for actuating is connected to the stationary counter-bearing on one side and to the sample on another side.

10. The device according to claim 1, comprising:
at least two means for actuating; and wherein
a first means for actuating is a servohydraulic, servomechanic and/or pneumatic actuator disposed in the load path between the bearing and the counter-bearing and is connected to the sample; and
at least one second means for actuating includes the solid body conversion material system, is disposed in the load path parallel or in series with the first actuator element and is coupled to the sample.

11. The device according to claim 1, wherein:
the at least one means for actuating includes a solid body conversion material for providing translatory deformations oriented in a direction of a load path and/or rotatory deformations relative to the load path, and wherein compressive and/or tensile forces and/or torsional forces and/or bending forces and/or shearing forces are introduced into the sample with the translatory deformations.

12. The device according to claim 1, comprising:
a loading or test frame and a second frame, the frames being spatially separated and wherein the first frame is the bearing and the second frame is the counter-bearing.

13. A device which provides dynamic load testing of a sample, comprising a bearing, to which the sample is connected, and a counter-bearing to which the sample is connected by of at least one means for actuating so that the at least one means for actuating introduces dynamic mechanical loads into the sample acting along a load path directed between the bearing and the counter-bearing and extending through the sample for subjecting the sample to vibrations produced by the at least one means for actuating which provides the dynamic load testing of the sample, wherein the at least one means for actuating includes a solid body conversion material system which undergoes deformations in response to application of energy, and wherein the deformations are at least one cause for the mechanical loads occurring within the sample during the dynamic testing thereof, and wherein
the at least one means for actuating, produces the vibrations for providing the dynamic load testing of the sample, comprises:
a base connecting element;
a load connecting element;
at least one support element;
at least one first energy conversion system including a solid body conversion material which extends between at least one application point lying on the base connecting element and at least one application point lying on the load connecting element;
at least one second energy conversion system including a solid body conversion material which extends between at least one application point lying on the support element and at least one application point lying on the load connecting element; and wherein
the base connecting element is connected to the at least one support element by at least one prestressing device providing a prestress exerted upon the first and the second energy conversion systems;
the load connecting element including a part thereof disposed in an intermediate space between the base connecting element and the support element and a part thereof disposed outside the intermediate space between the base connecting element and the support element; and
the base connecting element is connected to the counter-bearing and the load connecting element is connected to the sample by an interface including a rigid detachable connection.

14. The device according to claim 13, wherein
the solid body conversion material comprises a piezoceramic, an electrostrictive or magnetostrictive material.

15. The device according to claim 13, wherein
the solid body material comprises an electrostrictive, a magnetostrictive ceramic, a shape memory material, or a shape memory alloy material, or a combination thereof.

16. The device according to claim 13, wherein:
the bearing and the counter-bearing are spatially fixed; and
at least one means for actuating is connected to the stationary counter-bearing on one side and to the sample on another side.

17. The device according to claim 13, comprising:
at least two means for actuating; and wherein
a first means for actuating is a servohydraulic, servomechanic and/or pneumatic actuator disposed in the load path between the bearing and the counter-bearing and is connected to the sample; and
at least one second means for actuating includes the solid body conversion material system, is disposed in the load path parallel or in series with the first actuator element and is coupled to the sample.

18. The device according to claim 13, wherein:
the at least one means for actuating includes a solid body conversion material for providing translatory deformations oriented in a direction of a load path and/or rotatory deformations relative to the load path, and wherein compressive and/or tensile forces and/or torsional forces and/or bending forces and/or shearing forces are introduced into the sample with the translatory deformations.

19. The device according to claim 13, comprising:
a loading or test frame and a second frame, the frames being spatially separated and wherein the first frame is the bearing and the second frame is the counter-bearing.

20. The device according to claim 13, wherein:
the at least one prestressing device including an elastic tube enclosing the first and the second energy conversion systems.

* * * * *